(12) United States Patent
Freehauf

(10) Patent No.: US 7,671,034 B2
(45) Date of Patent: Mar. 2, 2010

(54) STABILIZED FORMULATION OF IVERMECTIN FEED PREMIX WITH AN EXTENDED SHELF LIFE

(75) Inventor: Keith Allan Freehauf, Stockton, NJ (US)

(73) Assignee: Merial Limited, Duluth, GA (US)

( * ) Notice: Subject to any disclaimer, the term of this patent is extended or adjusted under 35 U.S.C. 154(b) by 1013 days.

(21) Appl. No.: 10/790,489

(22) Filed: Mar. 1, 2004

(65) Prior Publication Data

US 2005/0136087 A1     Jun. 23, 2005

Related U.S. Application Data

(60) Provisional application No. 60/530,939, filed on Dec. 19, 2003.

(51) Int. Cl.
*A61K 31/70*     (2006.01)
(52) U.S. Cl. .................................................. 514/30
(58) Field of Classification Search ................ None
See application file for complete search history.

(56) References Cited

U.S. PATENT DOCUMENTS

| | | | |
|---|---|---|---|
| 4,199,569 A | 4/1980 | Chabala et al. .............. 424/180 |
| 4,283,400 A | 8/1981 | von Bittera et al. .......... 424/250 |
| 4,310,519 A | 1/1982 | Albers-Schonberg et al. .......................... 424/181 |
| 4,468,390 A | 8/1984 | Kitano .......................... 424/232 |
| 4,597,969 A | 7/1986 | Maxfield et al. .............. 424/157 |
| 4,939,166 A * | 7/1990 | Katoh et al. .................. 514/450 |
| 5,728,719 A | 3/1998 | Miller |
| 5,824,653 A | 10/1998 | Beuvry et al. .................. 514/30 |
| 5,891,491 A | 4/1999 | Owens et al. .................... 426/2 |
| 6,489,303 B2 * | 12/2002 | Jancys .......................... 514/30 |
| 6,548,478 B2 * | 4/2003 | Carson et al. .................. 514/9 |
| 7,001,889 B2 * | 2/2006 | Freehauf et al. ................ 514/29 |

FOREIGN PATENT DOCUMENTS

| | | |
|---|---|---|
| EP | 0 002 916 A2 | 7/1979 |
| EP | 0 007 812 A1 | 2/1980 |
| GB | 1390336 | 6/1973 |

* cited by examiner

*Primary Examiner*—Phyllis G. Spivack
(74) *Attorney, Agent, or Firm*—Judy Jarecki-Black; Merial Limited; Thomas Kowalski, Esq.

(57) ABSTRACT

The invention relates to a stabilized premix feed or feed-like formulation that has an extended shelf life due to a decrease of the degradates of the active ingredient by controlling the amount of an already existing stabilizer in the formulation. The feed premix is used in the treatment of parasites in mammals, in particular swine and horses. The invention further relates to a method to extend the shelf life of a stable premix feed or feed-like formulation for the treatment of parasite infestation in swine and horses comprising controlling the amount of an already existing antioxidant or stabilizer in the formulation to decrease or to prevent the formation of acid/base catalyzed decomposition of the active ingredient.

15 Claims, 5 Drawing Sheets

STABILIZED FORMULATION OF IVERMECTIN FEED PREMIX WITH AN EXTENDED SHELF LIFE

RELATED APPLICATIONS

This application claims priority to Provisional Application U.S. Ser. No. 60/530,939 entitled "Stabilized Formulation of Ivermerctin Feed Premix in Swine and Horses with an Extended Shelf Life and Method of Making the Same" filed Dec. 19, 2003.

FIELD OF THE INVENTION

The present invention relates to increasing the shelf life of drugs, which include anthelmintics and antiparasitic agents, formulated as premix feed or feed-like formulations. Particularly, the present invention provides for, inter alia, premix formulations and a method for increasing the shelf-life of avermectin and milbemycin derivatives, such as ivermectin, abamectin, emamectin, eprinomectin, doramectin, moxidectin, selamectin, and the like by controlling the amount of an already existing pharmaceutically or veterinary acceptable stabilizer in the premix in an amount effective to adjust the pH range to between about 4 to about 6 and therefore to decrease or to prevent the acid or base catalyzed decomposition in the premix of the avermectin or milbemycin compound, thereby extending the shelf life of the drug.

BACKGROUND OF THE INVENTION

Avermectin compounds are 16-membered macrocyclic lactones that are potent anthelmintic and antiparasitic agents against a wide range of internal and external parasites. The compounds which belong to this series are either natural products or are semi-synthetic derivatives thereof. The natural product avermectins are disclosed in U.S. Pat. No. 4,310,519 to Albers-Schonberg, et al., and the 22, 23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Furthermore, bioactive agents such as avermectins or ivermectin can be used in combination with other bioactive agents; and, with respect to avermectins, ivermectin, and bioactive agent combinations, reference is made to Kitano, U.S. Pat. No. 4,468,390, Beuvry et al., U.S. Pat. No. 5,824,653, von Bittera et al., U.S. Pat. No. 4,283,400, European Patent Application 0 007 812 A1, published Jun. 2, 1980, U.K. Patent Specification 1 390 336, published Apr. 9, 1975, European Patent Application 0002 916 A2, Ancare New Zealand Patent No. 237 086, Bayer New Zealand Patent 176193, published Nov. 19, 1975, inter alia. These prior publications and all other publications cited herein are expressly incorporated by reference.

A number of antiparasitic and anthelmintic products on the market contain ivermectin as an active ingredient. For example, IVOMEC Premix manufactured and sold by Merial is a free-flowing meal mixture containing 0.6% ivermectin for incorporation into animal feeding stuffs. It is indicated as an anthelmintic, insecticide and miticide against parasites in pigs and horses (the trade name in horses is Zimecterin EZ). IVOMEC Premix offers unsurpassed efficacy against mange mites, lice and gastrointestinal worms of pigs. Mixed into the feed it may be used in all classes of pigs and makes all round parasite control convenient and easy to apply. This compound treats a variety of parasites including gastro-intestinal worms such as *Ascaris suum, Hyostrongylus rubidus, Oesophagostomum* spp., *Strongyloides ransomi*, Lungworms such as *Metastrongylus* spp., Lice such as *Haematopinus suis*, Mange mites such as *Sarcoptes scabiei* var. suis. Ivomec premix for pigs given to pregnant sows before farrowing effectively controls transmission via the milk of *S. ransomi* to piglets. Avermectins are susceptible to both acid and base catalyzed decomposition. For example, the stability testing of Ivomec Swine Premix indicated that the shelf life of the drug decreases over time, possibly due to increase of ivermectin degradate resulted from acid/base catalyzed decomposition.

Some studies have shown that by incorporating stabilizers into the medicated feed of some animals, said stabilizers can prevent or decrease the degradation of the active ingredient and increase the shelf life of such compounds. For example, U.S. Pat. No. 5,891,491 to Owens et al. have used substituted 1,2-dihydroquinoline compound, in the feed of animals in an amount sufficient to increase the shelf life of the feed. Also, U.S. Pat. No. 4,597,969 to Maxfield et al. have disclosed a method of granulation involving polysaccharide gelling agents and metal salts for the stabilization of heat and or moisture sensitive drugs or food supplement such as efrotomycin, avermectins, milbemycins, moxidectin, and other drugs.

In light of the above, it is an object of the present invention to provide for a stabilized premix comprising at least one avermectin or milbemycin derivative for feed or feed-like formulations that exhibit improved shelf life by decreasing or preventing the formation of the degradates of the active ingredient. Moreover, it is an object of the invention to provide for a method of decreasing or preventing the formulation of degradates in a premix comprising at 1 least one a vermectin or milbemycin derivative. These and other objects will become apparent from the following Description of the Invention.

SUMMARY OF THE INVENTION

Figure 1:
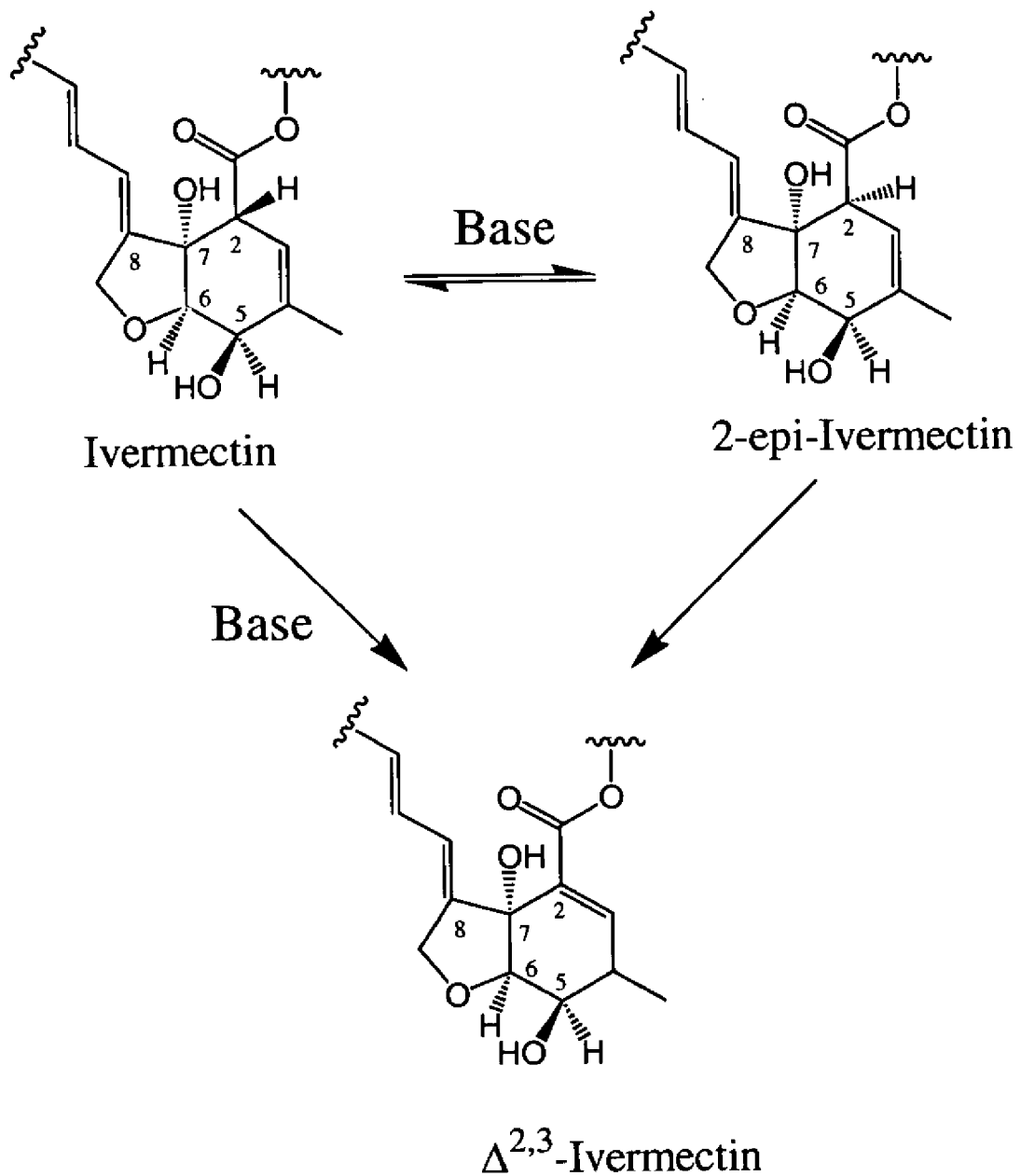
FIG. 1 depicts the degradation products which occur when ivermectin is subjected to base catalyzed degradation.

The invention provides for a stabilized premix feed or feed-like formulation that has an extended shelf life due to a decrease or prevention of the degradates of the active ingredients by controlling the amount of an already existing stabilizer in the formulation to adjust the pH of the premix to a range of about 4 to about 6. More specifically, the invention provides for, a stabilized premix feed or feed-like formulation for the treatment or prophylaxis of parasite infestation in swine and horses with an extended shelf life.

This invention also provides for a method to extend the shelf life of an active ingredient in a drug comprising controlling the amount of a stabilizer in the formulation of said drug to decrease or to prevent the formation of acid/base catalyzed decomposition of said active ingredient by adjusting the pH of the premix formulation to a range of about 4 to about 6.

These and other embodiments are disclosed or are obvious from and encompassed by, the following Detailed Description.

In this disclosure and in the appended claims, terms such as "comprising" and "comprises" and the like, have the meanings as ascribed to them in U.S. Patent base law. The terms "comprises" and "comprising" are open-ended and allow for the inclusion of additional ingredients or steps. Clearly, a stabilized premix which comprises an avermectin or milbemycin derivative that comprises an increased amount of stabilizer as well as a method for stabilizing premixes, thereby increasing their shelf life is a novel and basic feature of the invention. That the invention performs as herein described is surprising, unexpected and nonobvious.

DETAILED DESCRIPTION OF THE INVENTION

A premix for an animal feed that exhibits an extended shelf-life which comprises:
  a) a parasitically effective amount of at least one avermectin or milbemycin;
  b) a pharmaceutically acceptable excipient comprising:
    i) a pharmaceutically acceptable surfactant;
    ii) a pharmaceutically acceptable wax;
    iii) a pharmaceutically acceptable antioxidant;
    (iv) a pharmaceutically acceptable carrier vehicle wherein said vehicle is selected from the group consisting of fine corn cobs, corn meal, citrus meal, fermented residues, ground oyster shells, wheat shorts, molasses solubles, bean mill feed, soy grits, crushed limestone and dried grains;
  c) a pharmaceutically acceptable amount of a pharmaceutically acceptable stabilizer in an amount effective to adjust the pH of the formulation to a range of about 4 about 6 to decrease or to prevent the acid or base catalyzed decomposition in the premix of the at least one avermectin or milbemycin compound; and
  d) optionally, an effective amount of at least one insect growth regulating compound.

A more preferred embodiment of the invention is a premix which comprises:
  a) about 0.04 to about 5% (w/w) of at least one avermectin compound;
  b) a pharmaceutically acceptable excipient comprising:
    i) about 5 to about 15% (w/w) of a surfactant wherein said surfactant is selected from the group consisting of polyoxyl 40 hydrogenated castor oil, PEG-50 castor oil, PEG-60 corn glyceride, PEG-60 almond oil, PEG-40 palm kernel oil, and PEG-60 corn oil;
    ii) about 5 to about 25% (w/w) of a wax wherein said wax is selected from the group consisting of distilled monoglycerides, glyceryl tribehenate, glyceryl trimyristate, and hydrogenated coco-glycerides;
    iii) about 0.1 to about 2% (w/w) of an antioxidant wherein said antioxidant is selected from the group consisting of butylated hydroxyanisole, butylated hydroxytoluene, ascorbic acid, sodium metabisulphite, propyl gallate, sodium sulfite, sodium thiosulphate, and a mixture thereof;
    iv) about 60 to about 80% (w/w) of a pharmaceutically acceptable carrier vehicle wherein said carrier vehicle is selected from the group consisting of fine ground corn cobs, crushed limestone, and dried grains,
  c) a pharmaceutically acceptable amount of a pharmaceutically acceptable stabilizer in an amount effective to adjust the pH of the premix formulation to a range of about 4 to about 6 in order to decrease the acid or base catalyzed decomposition of the at least one avermectin or milbemycin compound said stabilizer is selected from a group consisting of citric acid, gallic acid, maleic acid, glycolic acid, thioglycolic acid, alginic acid and a mixture thereof; and
  d) optionally, an effective amount of at least one insect growth regulating compound selected from the group consisting of azadirachtin, diofenolan, fenoxycarb, hydroprene, kinoprene, methoprene, pyriproxyfen, tetrahydroazadirachtin, and 4-chloro-2-(2-chloro-2-methylpropyl)-5-(6-iodo-3-pyridylmethoxy)pyridizin-3 (2H)-one chlorfluazuron, cyromazine, diflubenzuron, fluazuron, flucycloxuron, flufenoxuron, hexaflumuron, lufenuron, tebufenozide, teflubenzuron, and triflumuron and a mixture thereof.

Another embodiment of this invention provides for a method for extending the shelf life of a premix for an animal feed comprising at least one pharmaceutically active compound wherein said pharmaceutically active compound is an avermectin or milbemycin compound said method comprises controlling the amount of a stabilizer in an amount effective to adjust the pH of said premix formulation to a range of about 4 to about 6 in order to decrease the acid or base catalyzed decomposition in the premix of the avermectin or milbemycin compound.

Avermectins and milbemycins are susceptible to both acid and base catalyzed degradation. The macrocyclic lactone of all avermectins has at carbon 13 an α-L-oleandrosyl-α-L-oleandrosyloxy substituent which is a 2-deoxy sugar glycoside; and as such it is relatively sensitive to acid hydrolysis or alcoholysis. A solution of ivermectin in methanol containing a strong acid such as 1% sulfuric acid readily gives a good yield of the aglycone after 16 to 24 hours at room temperature. These procedures readily yield the monosaccharides of ivermectin and Avermectin $B_1$ and the aglycone of ivermectin.

Figure 2:
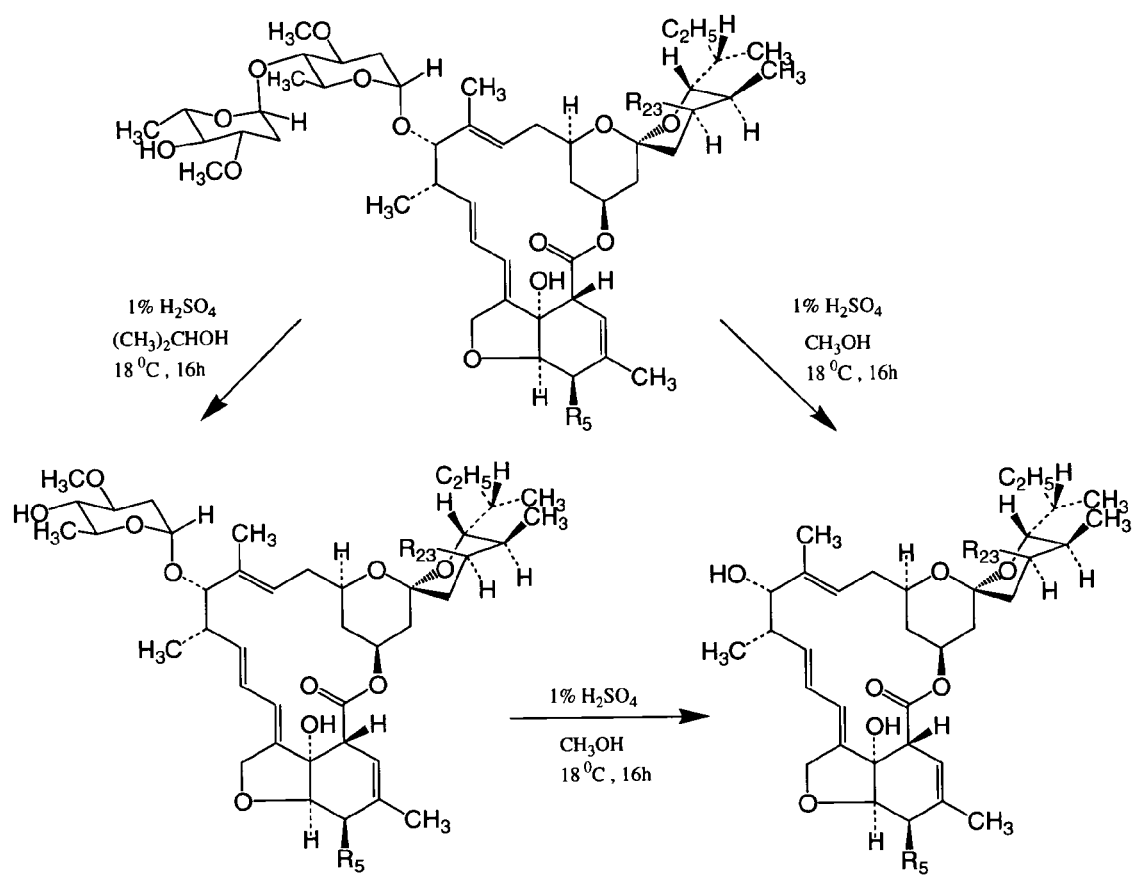
FIG. 2 depicts the degradation products which occur when ivermectin is subjected to acid catalyzed degradation.
Figure 3:
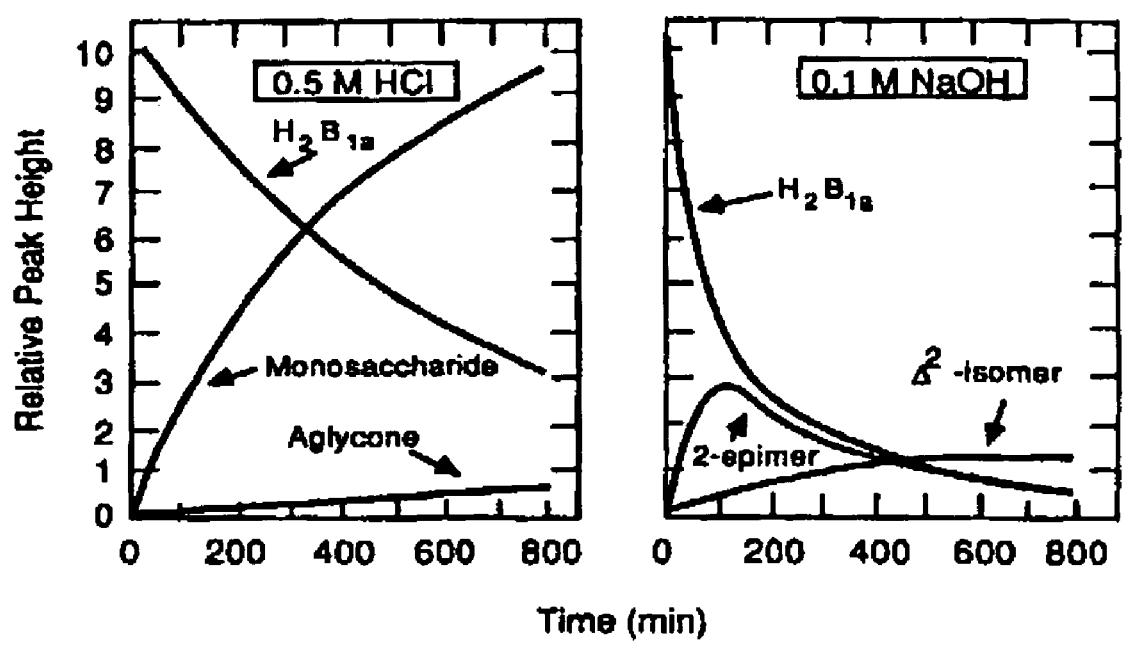
FIG. 3 depicts the reaction rate profile of the acid and base catalyzed decomposition of ivermectin.

Also, the two degradates, 2-epimer and the $\Delta^{2,3}$ isomer of avermectin and mylbemycins, are formed in the presence of a base. For example, decrease in ivermectin as the active ingredient in Premix formulations is caused by formation of ivermectin degradate 2-epimer, which is a product of base catalyzed degradation in ivermectin. FIG. 1 illustrates the two degradates, 2-epimer and the $\Delta^{2,3}$ isomer, that are formed in the presence of a strong base. FIG. 2 illustrates the two degradates, monosaccharide and the aglycone, that are formed in the presence of a strong acid. FIG. 3 illustrates the reaction rate profile of acid and base catalyzed hydrolysis of ivermectin.

The addition of an organic or inorganic base to the formulation could prevent or decrease the amount of acid catalyzed degradates of the avermectins or milbemycins. Similarly, the addition of an organic or inorganic acid to the formulation could prevent or decrease the amount of base catalyzed degradates of avernectins. The modification in the amount of the organic acid already present in the excipient of the present formulation, is an object of this instant invention. Thus, advantageously, the invention provides for a stabilized premix feed or feed-like formulation in the treatment or prophylaxis of parasites in mammals, and in particular swine and horses with an extended shelf life, by decreasing or preventing the degradation of the active ingredient due to the modification of the amount of the already existing stabilizer in the formulation that would adjust the pH of the premix formulation to a range of about 4 to about 6. In particular the modification in the amount of the existing stabilizer in the formulation comprises a small increase in the amount of such stabilizer in the formulation. That small increases could achieve these results is unexpected.

Stabilizers that decrease or prevent the acid or base catalyzed decomposition of an avermectin or milbemycin in a premix include and could be acids or bases. Organic acids and bases used in this instant invention could be either anhydrous or hydrated (mono-, di-, tri-, tetra-, penta-, hexa, hepta, etc.). The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary-acceptable aliphatic, alicyclic and aromatic carboxylic acids, dicarboxylic acids, tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid, thioglycolic acid and lactic acid, chloroacetic acid, benzoic acid, methane sulfonic acid, and salicylic acid. Examples of dicarboxylic acids include oxalic acid, malic acid, succinic acid, tartaric acid and maleic acid. An example of a tricarboxylic acid is citric acid. Fatty acids include all pharmaceutically or veterinary-acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid, gallic acid, salicylic acid, malonic acid, ascorbic acid, isoascorbic acid, or a mixture thereof.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

Antioxidants used in this instant invention are well known in the art and particularly preferred antioxidants include but are not limited to butylated hydroxyanisole, butylated hydroxytoluene, ascorbic acid, sodium metabisulphite, propyl gallate, sodium thiosulphate or a mixture thereof. Preferably the antioxidants and/or stabilizers used in this invention are solubilized in suitable organic solvents well known in the art. Examples of organic solvents include but are not limited to straight chain or branched alcohols such as methyl alcohol, ethyl alcohol, propyl alcohol, butyl alcohol, isopropyl alcohol and the like, other solvents include but are not limited to benzylbenzoate, Crodamol, miglyol, ethylene glycol, propylene glycol, polyethylene glycol, glycerol, glycerol formal, N-methylpyrrolidone, sorbitol, pentaerythriol, and the like.

The determination of an amount of stabilizer effective to decrease or prevent the acid or base catalyzed degradation that brings the pH range of the instant premix formulation to pH of about 4 to about 6 and thereby extends the shelf-life of the product by six to twenty-four months, more preferably by nine to eighteen months and most preferably nine to twelve months, is made by increasing a small amount of stabilizers in addition to that amount normally added in the art. Comparisons are made with respect to IVOMEC Premix. Preferred amounts of the stabilizer range from about 0.3 to about 1.5% (w/w), with about 0.3 to about 1.2% (w/w) being more preferred. Most preferably the increased amount of stabilizer is about 0.4 to about 0.5% (w/w).

This invention includes all avermectin derivatives known in the art. Especially preferred stabilized premix feed or feed-like formulations comprising avermectin or milbemycin derivatives include but are not limited to milbemycin, milbemycin oxime, abamectin, moxidectin, emamectin, eprinomectin, doramectin, selemectin and ivermectin.

In a most preferred embodiment the instant invention provides for a stabilized premix feed or feed-like formulation for the treatment or prophylaxis of parasite infestation in swine and horses with an extended shelf life comprising:
 (a) 0.62% (w/w) of ivermectin,
 (b) a pharmaceutically or veterinary acceptable excipient consisting of:
  (i) 8.00% (w/w) of polyoxyl 40 hydrogenated castor oil;
  (ii) 20.80% (w/w) of distilled monoglycerides;
  (iii) 0.13% (w/w) of butylated hydroxyanisole, propyl gallate, and 0.02% (w/w) of anhydrous citric acid in 0.35% (w/w) of propylene glycol
  (iv) 69.6% (w/w) of fine ground corn cobs; and
 (c) 0.48% (w/w) increase of anhydrous citric acid.

The term "excipient" contemplates all ingredients in the formulation that are not part of the active ingredients. An excipient may include but is not limited to solvents, waxes, antioxidants, stabilizers, solubilizers, liquid or solid vehicle carriers, anticaking agents and the like.

In addition, the compounds of the present invention are administered via an animal feedstuff, hence, they are intimately dispersed in the feed or used as a top dressing or in the form of pellets which may then be added to the finished feed or optionally fed separately.

When the compounds described herein are administered as components of the feed of the animals, or dissolved or suspended in the drinking water, compositions are provided in which the active compounds are intimately dispersed in an inert carrier or diluent. Inert carrier means one that will not react with the antiparasitic agent and one that may be administered safely to animals. Preferably, a carrier for feed administration is one that is, or may be, an ingredient of the animal ration.

Suitable compositions include feed premixes or supplements in which the instant compounds are present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soy grits, crushed limestone and the like. The compounds of the present invention are intimately dispersed throughout the carrier by methods such as grinding, stirring, milling or tumbling.

Examples of IGR compounds which may be used in the formulation of the present invention include compounds which mimic juvenile hormones and chitin-synthesis inhibitors. Preferred compounds that mimic juvenile hormones include azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3(2H)-one pyridylmethoxy)pyridizin-3(2H)-one. Preferred and chitin-synthesis inhibitors include chlorfluazuron, cyromazine, diflubenzuron, fluazuron, flucycloxuron, flufenoxuron, hexaflumuron, lufenuron, tebufenozide, teflubenzuron, triflumuron. These compounds are defined by their international common name (The Pesticide Manual, $10^{th}$ edition, 1994, Ed. Clive Tomlin, Great Britain).

Chitin-synthesis inhibitors also include compounds such as 1(2,6-difluorobenzoyl)-3-(2-fluoro-4-((trifluoromethyl))phenylurea, 1-(2,6-difluorobenzoyl)-3-(2-fluoro-4-(1,1,2,2-tetrafluoroethoxy))phenylurea and 1-(2,6-difluorobenzoyl)-3-(2-fluoro-4-trifluoro-methyl)phenylurea Novaluron (Isagro, Italian company) is also an example of an IGR compound.

Preferred IGR compounds include methoprenes, pyriproxyfens, hydroprene, cyromazine, lufenuron, 1-(2,6-difluorobenzoyl)-3-(2-fluoro-4-(trifluoromethyl)phenylurea and novaluron.

Antioxidant used in the present invention are well known in the art. Examples of antioxidants are but not limited to alpha tocopheral, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The waxes in the instant invention are used to protect the active ingredient. Examples of waxes include distilled monoglycerids, glycerol tribehenate, glyceryl trimyristate and hydrogenated coco-glycerides.

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, soybean oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol M40), and PEG-20 almond glycerides (Crovol A40).

The following example is intended to illustrate the preparation of the compositions of the invention but it is not to be construed as limiting the scope thereof.

EXAMPLE 1

Preparation of the Stabilized Premix Feed Comprising Ivermectin as an Active Ingredient Polyoxyl 40 hydrogenated castor oil was heated to 75-85° C. While maintaining this temperature, distilled monoglycerides was added to it. Once a homogeneous solution was achieved, BHA, n-propyl gallate, anhydrous citric acid and propylene glycol, were added to the mixture, followed by the addition of ivermectin. The temperature of the solution was then maintained at 75-85° C. In a suitable size mixer, fine ground corncobs were charged and with continuous agitation the temperature was raised to 75-85° C. The hot ivermectin solution was then transferred to the heated corncobs, and the mixture was mixed until it became homogeneous. The vessel was then cooled with continuous agitation until the product temperature was below 40° C.

TABLE I shows the amount of the of the ingredients used to prepare the premix formulation of the instant invention:

| INGREDIENT | COMPOSITION (w/w %) |
|---|---|
| Ivermectin | 0.62 |
| Polyoxyl 40 Hydrogenated Castor Oil | 8.00 |
| Distilled Monoglycerides | 20.80 |
| Butylated Hydroxyanisole | 0.10 |
| Propyl Gallate | 0.03 |
| Anhydrous Citric Acid | 0.02 |
| Propylene Glycol | 0.35 |
| Additional Anhydrous Citric Acid | 0.48 |
| Fine Ground Corn Cobs | QS 100 |

Evaluation of stability studies for product without citric acid addition revealed that Ivermectin Assay steadily decreased with time, when stored under the VICH (International Cooperation on Harmonization of Technical Requirements for Registration of Veterinary Products) conditions. Data collected after 9 months stability study for product with additional amount of citric acid demonstrated better stability. Results are shown in Table II.

TABLE II

Comparison of the stability of ivermectin at different temperature and relative humidity with and without addition of increased citric acid over a period of 9 month.

| | Without Addition of Increased Citric Acid | | With Addition of Increased Citric Acid | | |
|---|---|---|---|---|---|
| | | Ivermectin Assay (average) | | Ivermectin Assay (average) | |
| Assay No. | Time, months | 25° C./60% RH | Time, months | 25° C./ 60% RH | 30° C./ 60% RH | 40° C./ 75% RH |
| 1 | 0 | 99.0 | 0 | 101.4 | 101.4 | 101.4 |
| | 1 | 98.7 | — | — | — | — |
| | 3 | 97.9 | 3 | 101.2 | 99.9 | 98.9 |
| | 6 | 98.7 | 6 | 104.5 | 100.6 | 96.2 |
| | | | 9 | 104.3 | 100.2 | — |

TABLE II-continued

Comparison of the stability of ivermectin at different temperature and relative humidity with and without addition of increased citric acid over a period of 9 month.

| | Without Addition of Increased Citric Acid | | With Addition of Increased Citric Acid | | |
|---|---|---|---|---|---|
| | | Ivermectin Assay (average) | | Ivermectin Assay (average) | |
| Assay No. | Time, months | 25° C./60% RH | Time, months | 25° C./ 60% RH | 30° C./ 60% RH | 40° C./ 75% RH |
| 2 | 0 | 100.8 | 0 | 100.9 | 100.9 | 100.9 |
| | 3 | 99.8 | 3 | 101.6 | 100.9 | 98.6 |
| | 6 | 97.4 | 6 | 101.8 | 101.3 | 97.4 |
| | 8 | 97.7 | 9 | 103.5 | 99.0 | — |
| | 12 | 98.5 | | | | |
| 3 | 0 | 99.2 | 0 | 101.0 | 101.0 | 101.0 |
| | 13 | 97.4 | 3 | 101.9 | 102.5 | 100.1 |
| | 19 | 95.5 | 6 | 105.0 | 103.1 | 98.4 |
| | 24 | 93.0 | 9 | 100.1 | 101.3 | — |
| | 29 | 92.4 | | | | |
| 4 | 0 | 98.3 | | | | |
| | 13 | 97.2 | | | | |
| | 19 | 95.7 | | | | |
| | 24 | 92.0 | | | | |
| | 29 | 92.5 | | | | |
| 5 | 0 | 98.2 | | | | |
| | 13 | 98.2 | | | | |
| | 24 | 96.8 | | | | |

Table III compares the percentages of the ivermectin and ivermectin degradates over a 1 month period, under various storage conditions, when different percentages of additional anhydrous citric acid are added to the formulation that already contains 0.02% anhydrous citric acid.

TABLE III

| Assay No. | % of added Citric Acid | Storage Conditions | Ivermectin % | 2-epimer % | Monosaccharide |
|---|---|---|---|---|---|
| 1 | 0.28 | 5 C. | 0.59 | 0 | 0.10 |
| | | 40 C./75% RH | 0.55 | 0.17 | 0.13 |
| | | 50 C./amb | 0.59 | 0.29 | 0.13 |
| 2 | 0.38 | 5 C. | 0.55 | 0 | 0.13 |
| | | 40 C./75% RH | 0.53 | 0.15 | 0.17 |
| | | 50 C./amb | 0.56 | 0.26 | 0.17 |
| 3 | 0.3 | 5 C. | 0.57 | 0 | 0.17 |
| | | 40 C./75% RH | 0.55 | 0.14 | 0.19 |
| | | 50 C./amb | 0.58 | 0.24 | 0.23 |
| 4 | 0.48 | 5 C. | 0.58 | 0 | 0.23 |
| | | 40 C./75% RH | 0.56 | 0.12 | 0.26 |
| | | 50 C./amb | 0.59 | 0.22 | 0.30 |
| 5 | 0.73 | 5 C. | 0.56 | 0 | 0.23 |
| | | 40 C./75% RH | 0.54 | 0 | 0.31 |
| | | 50 C./amb | 0.55 | 0.19 | 0.37 |

*RH: relative humidity
*Amb: ambient temperature

Table IV. Compares the percentages of the ivermectin (label claim) and ivermectin degradates in the formulation up to 18 months in 3 different assays where the total amount of citric acid in the formulation is about 0.6%.

TABLE IV

| Storage Condition | Time (Months) | Assay (Ivermectin) 95.0-105.0% of Label Claim Label Claim 0.6% (w/w) | Ivermectin Related Substances | | | | | |
|---|---|---|---|---|---|---|---|---|
| | | | Max. total 2.5% $H_2B_{1a}$ (delta) 2,3 + $H_4B_{1a}$ isomers | Max. 1.0% 2-epimer | Max. 1.0% Aglycone | Max. 1.0% Monosaccharide | Max. 1.0% Unspecified (each individual) | Max. 5% Total degradates |
| ASSAY No. 1 | | | | | | | | |
| 25° C./60% RH | 3 | 101.2-101.1 | 1.85 | 0 | 0.1 | 0.1 | Max 0.3% | 2.8 |
| | 6 | 104.7-104.3 | 1.8 | 0 | 0 | 0.15 | Max 0.3% | 2.95 |
| | 9 | 101.1-101.4 | 1.8 | 0.1 | 0.2 | 0.2 | Max 0.3% | 2.7 |
| | 12 | 98.3-99.4 | 1.8 | 0.15 | 0 | 0.15 | Max 0.4% | 3.0 |
| | 18 | 100.2-99.9 | 1.8 | 0.2 | 0 | 0.2 | Max 0.5% | 3.75 |

TABLE IV-continued

| | | Assay (Ivermectin) | Ivermectin Related Substances | | | | | |
|---|---|---|---|---|---|---|---|---|
| Storage Condition | Time (Months) | 95.0-105.0% of Label Claim Label Claim 0.6% (w/w) | Max. total 2.5% $H_2B_{1a}$ (delta) 2,3 + $H_4B_{1a}$ isomers | Max. 1.0% 2-epimer | Max. 1.0% Aglycone | Max. 1.0% Monosaccharide | Max. 1.0% Unspecified (each individual) | Max. 5% Total degradates |
| 30° C./60% RH | 3 | 99.3-100.4 | 1.8 | 0 | 0.15 | 0.1 | Max 0.3% | 2.7 |
| | 6 | 101.0-100.2 | 1.8 | 0.2 | 0 | 0.2 | Max 0.3% | 2.7 |
| | 9 | 100.6-99.7 | 1.9 | 0.3 | 0.2 | 0.2 | Max 0.3% | 2.7 |
| | 12 | 98.4-98.5 | 1.8 | 0.4 | 0 | 0.2 | Max 0.3% | 3.4 |
| | 18 | 97.5-98.3 | 1.9 | 0.6 | 0 | 0.3 | Max 0.5% | 4.7 |
| 40° C./75% RH | 3 | 99.5-98.2 | 1.8 | 0.3 | 0.2 | 0.2 | Max 0.3% | 2.7 |
| | 6 | 96.4-96.0 | 1.85 | 0.8 | 0 | 0.4 | Max 0.3% | 3.9 |
| ASSAY No. 2 | | | | | | | | |
| 25° C./60% RH | 3 | 101.8-101.3 | 1.8 | 0 | 0 | 0.1 | Max 0.35% | 2.7 |
| | 6 | 101.8-101.8 | 1.8 | 0 | 0 | 0.15 | Max 0.4% | 3.2 |
| | 9 | 103.3-103.6 | 1.8 | 0.1 | 0 | 0.15 | Max 0.35% | 2.9 |
| | 12 | 99.3-98.5 | 1.7 | 0.15 | 0.1 | 0.2 | Max 0.55% | 3.2 |
| | 18 | 98.9-98.8 | 1.8 | 0.2 | 0 | 0.25 | Max 0.5% | 3.5 |
| 30° C./60% RH | 3 | 101.3-100.5 | 1.8 | 0 | 0 | 0.15 | Max 0.35% | 2.7 |
| | 6 | 101.6-100.9 | 1.8 | 0.2 | 0 | 0.2 | Max 0.35% | 3.0 |
| | 9 | 98.9-99.1 | 1.8 | 0.3 | 0.1 | 0.2 | Max 0.35% | 3.0 |
| | 12 | 98.5-99.1 | 1.8 | 0.4 | 0 | 0.2 | Max 0.5% | 3.5 |
| | 18 | 97.7-98.2 | | 0.6 | 0 | 0.3 | Max 0.5% | 4.7 |
| 40° C./75% RH | 3 | 98.6-98.6 | 1.8 | 0.35 | 0 | 0.2 | Max 0.3% | 3.0 |
| | 6 | 97.5-97.2 | 1.8 | 0.7 | 0 | 0.4 | Max 0.4% | 3.9 |
| ASSAY No. 3 | | | | | | | | |
| 25° C./60% RH | 3 | 102.0-101.8 | 1.8 | 0 | 0 | 0.1 | Max 0.3% | 2.7 |
| | 6 | 105.0-105.3 | 1.8 | 0 | 0 | 0.15 | Max 0.3% | 3.0 |
| | 9 | 100.7-99.5 | 1.85 | 0 | 0 | 0.2 | Max 0.3% | 2.7 |
| | 12 | 101.4-102.1 | 1.8 | 0.1 | 0.1 | 0.15 | Max 0.6% | 3.2 |
| | 18 | 99.9-99.9 | 1.8 | 0.2 | 0 | 0.2 | Max 0.5% | 3.5 |
| 30° C./60% RH | 3 | 103.1-101.8 | 1.8 | 0 | 0 | 0.1 | Max 0.3% | 3.0 |
| | 6 | 102.6-103.6 | 1.8 | 0.1 | 0 | 0.2 | Max 0.3% | 3.0 |
| | 9 | 101.5-101.1 | 1.8 | 0.2 | 0.1 | 0.2 | Max 0.3% | 2.7 |
| | 12 | 99.9-100.6 | 1.8 | 0.3 | 0.1 | 0.2 | Max 0.5% | 3.5 |
| | 18 | 98.9-99.4 | 1.9 | 0.5 | 0 | 0.3 | Max 0.5% | 4.7 |
| 40° C./75% RH | 3 | 99.1-101.0 | 1.9 | 0.3 | 0 | 0.2 | Max 0.3% | 3.0 |
| | 6 | 98.7-98.1 | 1.9 | 0.6 | 0 | 0.4 | Max 0.3% | 4.0 |

These results confirm the improved stability profile of the instant invention with an average ivermectin assay result well above the 95% specification limit after 18 months of storage at both 25° C./60% RH and 30° C./60% RH. In addition the rate of degradation of ivermectin is better controlled with a total amount of degradates below the 5% specification limit which is the maximum level of degradates allowed for this instant invention and is the currently approved specification at shelf-life.

Figure 4:
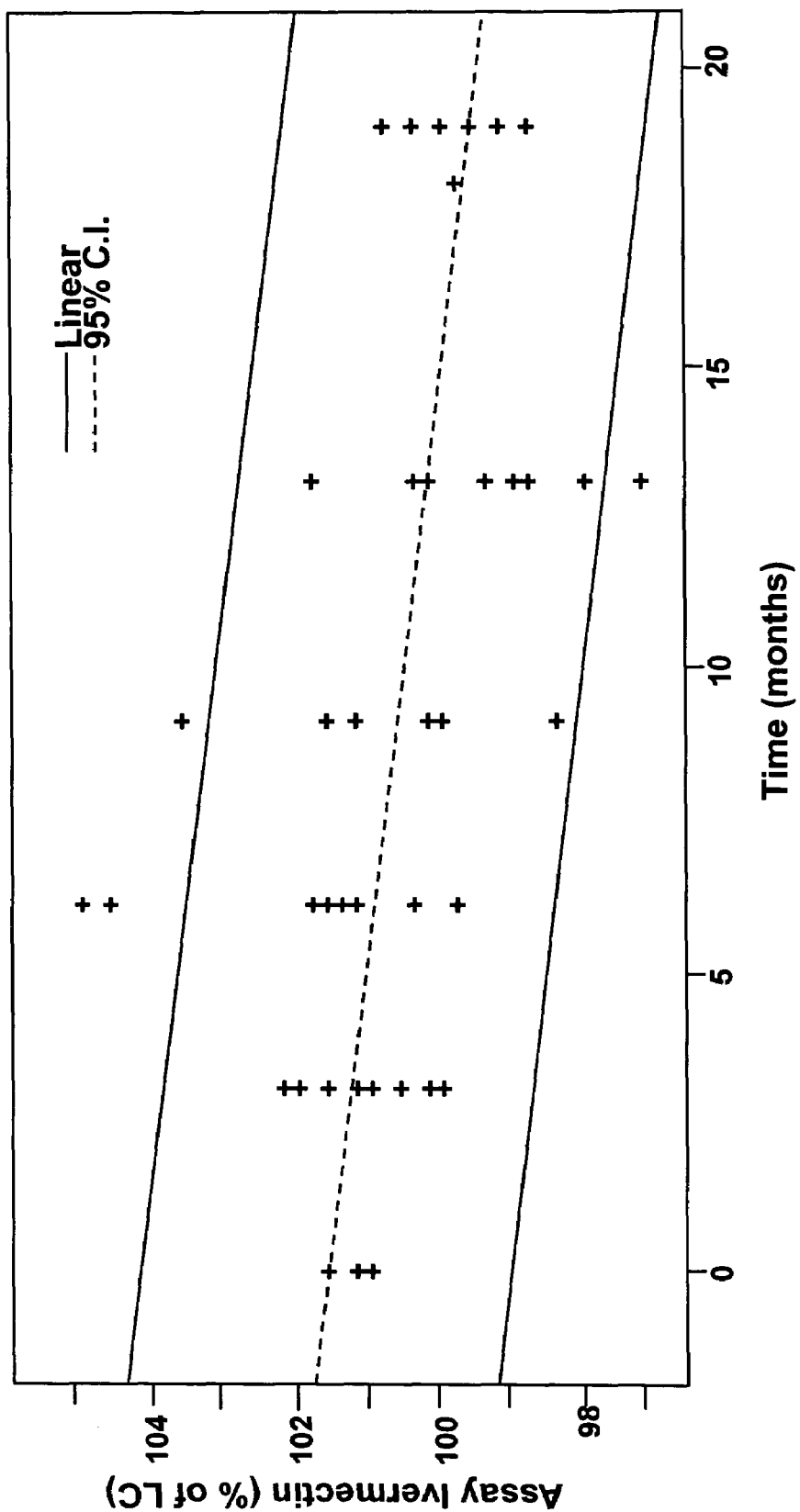
FIG. 4 depicts the decrease of ivermectin in the formulation over 18 months when stored under 25° C./60% relative humidity storage condition.
Figure 5:
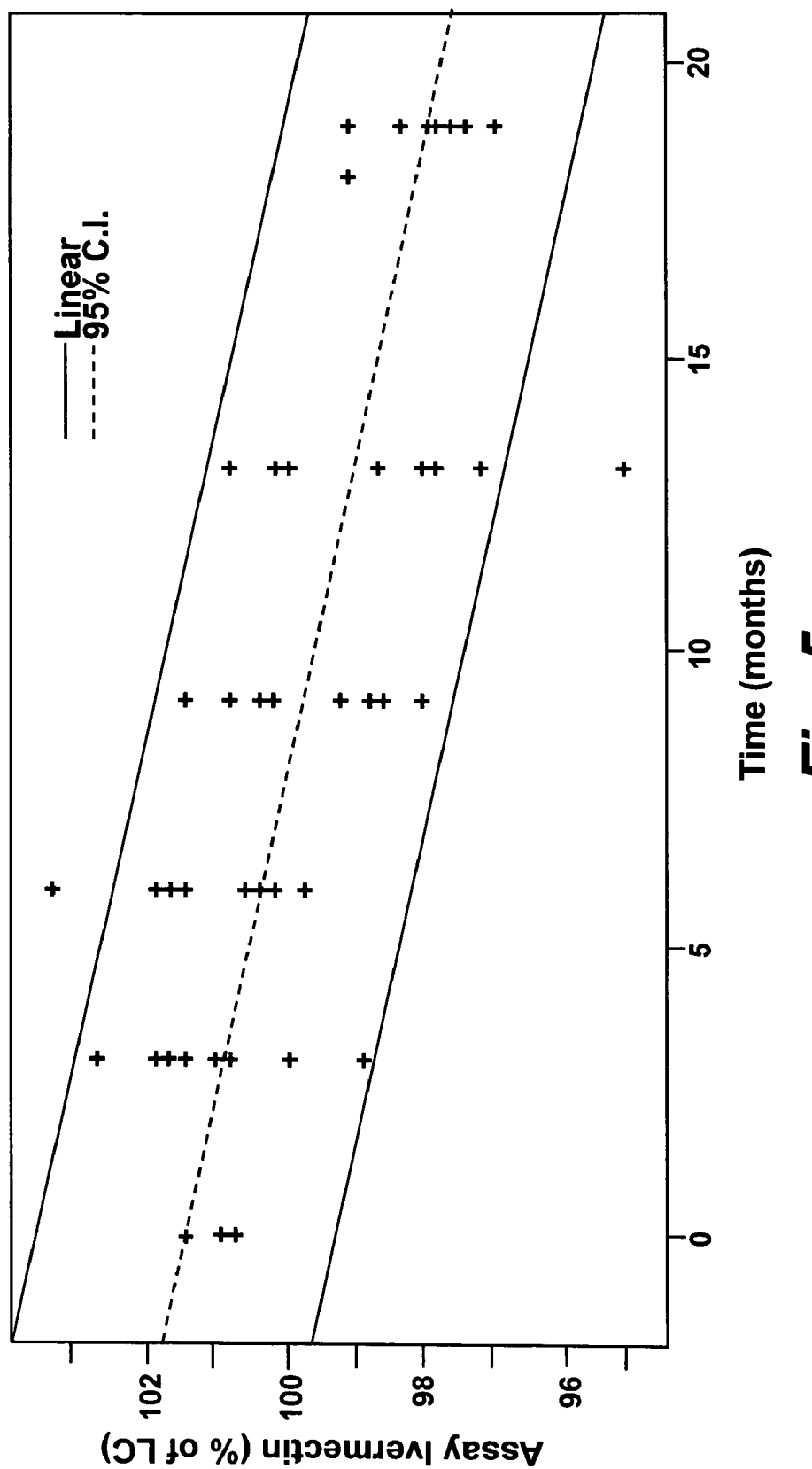
FIG. 5 depicts the decrease of ivermectin in the formulation over 18 months when stored under 30° C./60% relative humidity storage condition.

By applying a Linear Regression Model to the data shown in Table IV. and FIGS. 4 and 5, one obtains the relationship between Ivermectin content (Y) and the shelf-life of the drug (X) expressed in Months as follows: Y=101.4714+(−9.789569E-02)X at 25° C./60% RH storage condition and Y=101.4181+(−0.1805759)X at 30° C./60% RH storage condition respectively. The graphs in FIGS. 4 and 5 show that the content of ivermectin stays well above the 95% limit which is the currently approved specification at shelf-life even after 24 months.

The above description of the invention is intended to be illustrative and not limiting. Various changes or modifications in the embodiments described herein may occur to those skilled in the art. These can be made without departing from the scope and spirit of the invention.

The invention claimed is:

1. A premix for an animal feed that exhibits an extended shelf-life consisting essentially of:

a) about 0.04 to about 0.7% (w/w) of at least one avermectin compound;

b) a pharmaceutically acceptable excipient comprising:
   i) about 5 to about 15% (w/w) of a surfactant wherein said surfactant is selected from the group consisting of polyoxyl 40 hydrogenated castor oil, PEG-50 castor oil, PEG-60 corn glyceride, PEG-60 almond oil, PEG-40 palm kernel oil, and PEG-60 corn oil;
   ii) about 15 to about 25% (w/w) of a wax wherein said wax is selected from the group consisting of distilled monoglycerides, glyceryl tribehenate, glyceryl trimyristate, and hydrogenated coco-glycerides;
   iii) about 0.1 to about 2% (w/w) of an antioxidant wherein said antioxidant is selected from the group consisting of butylated hydroxyanisole, butylated hydroxytoluene, ascorbic acid, sodium metabisulphite, propyl gallate, sodium thiosulphate, propylene glycol, citric acid, anhydrous citric acid and a mixture thereof;
   iv) about 60 to about 80% (w/w) of a pharmaceutically acceptable carrier vehicle wherein said carrier vehicle is selected from the group consisting of fine ground corn cobs, crushed limestone, and dried grains;

c) about 0.3 to about 1% (w/w) of an additional amount of a pharmaceutically acceptable acid stabilizer effective to decrease the acid or base catalyzed decomposition of the at least one avermectin compound, and;

d) optionally, an effective amount of at least one insect growth regulating compound.

2. The premix according to claim 1, wherein the avermectin is selected from the group consisting of ivermectin, abamectin, emamectin, eprinomectin, doramectin, moxidectin, and selamectin.

3. The premix according to claim 1, wherein the insect growth regulating compound is selected from the group consisting of azadirchtin, diofenolan, fenoxycarb, hydroprene, kinoprene, methoprene, pyriproxyfen, tetrahydroazadirachtin, and 4-chloro-2-(2-chloro-2-methylpropyl)-5-(6-iodo-3-pyridylmethoxy)pyridizin-3(2H)-one.

4. The premix according to claim 1 wherein the insect growth regulating compound is one that inhibits chitin synthesis.

5. The premix according to claim 4, wherein the insect growth regulating compound is selected from the group consisting of chlorfluazuron, cyromazine, diflubenzuron, fluazuron, flucycloxuron, flufenoxuron, hexaflumuron, lufenuron, tebufenozide, teflubenzuron, and triflumuron.

6. The premix according to claim 1 wherein the insect growth regulating compound is selected from the group consisting of methoprenes, pyriproxyfens, hydrofene, cyromazine, lufenuron, 1-(2,6-difluorobenzoyl)-3-(2-fluoro-4-(trifluoromethyl)phenylurea, novaluron and a mixture thereof.

7. The premix formulation according to claim 1 wherein the shelf-life is extended from 6 to 24 months.

8. The premix formulation according to claim 1 wherein the shelf-life is extended from 9 to 18 months.

9. The premix formulation according to claim 1 wherein the stabilizer is selected from a group consisting of: anhydrous citric acid, glycolic acid, thioglycolic acid, gallic acid, maleic acid, and a mixture thereof.

10. The premix formulation according to claim 1 wherein the stabilizer is anhydrous citric acid.

11. The premix according to claim 1, wherein the amount of the added stabilizer is between about 0.3 to about 0.7% (w/w).

12. The premix according to claim 1 wherein the amount of the added stabilizer is about 0.4 to about 0.5% (w/w).

13. The premix according to claim 1 wherein the animal feed is swine feed or horse feed.

14. The premix according to claim 1 consisting essentially of:
a) about 0.04 to about 0.7% (w/w) ivermectin;
b) a pharmaceutically acceptable excipient comprising:
  i) about 5 to about 15% (w/w) polyoxyl 40 hydrogenated castor oil;
  ii) about 15 to about 25% (w/w) distilled monoglycerides;
  iii) about 0.1 to about 2% (w/w) of an antioxidants wherein said antioxidants are selected from the group consisting of butylated hydroxyanisole, propyl gallate, propylene glycol, citric acid, anhydrous citric acid and a mixture thereof;
  iv) about 60 to about 80% (w/w) fine ground corn cobs;
c) about 0.3 to about 1% (w/w) of additional anhydrous citric acid in order to decrease the acid or base catalyzed decomposition of the ivermectin compound, and;
d) optionally, a effective amount of at least one insect growth regulating compound selected from the group consisting of methopenes, pyriproxyfens, hydrofene, cyromazine, lufenuron, 1-(2,6-difluorobenzoyl)-3-(2-fluoro-4-(trifluoromethyl)phenylurea, novaluron and a mixture thereof.

15. A premix for an animal feed that exhibits an extended shelf-life consisting essentially of:
a) about 0.62% (w/w) ivermectin;
b) a pharmaceutically acceptable excipient comprising:
  i) about 8% (w/w) polyoxyl 40 hydrogenated castor oil;
  ii) about 21% (w/w) distilled monoglycerides;
  iii) about 0.5% (w/w) butylated hydroxyanisole, propyl gallate, anhydrous citric acid, propylene glycol, or a mixture thereof
  iv) qs 100% (w/w) fine ground corn cobs;
c) about 0.48% (w/w) increase of anhydrous citric acid, and;
d) optionally, a effective amount of at least one insect growth regulating compound selected from the group consisting of methoprenes, pyriproxyfens, hydrofene, cyromazine, lufenuron, 1-(2,6-difluorobenzoyl)-3-(2-fluoro-4-(trifluoromethyl)phenylurea, novaluron and a mixture thereof.

* * * * *